United States Patent [19]

Farfel

[11] Patent Number: 5,755,763
[45] Date of Patent: May 26, 1998

[54] PACEMAKER CONNECTOR WITH SEALABLE ACCESS OPENINGS AND METHODS FOR ITS USE

[76] Inventor: Bernard Farfel, 5521 Shadowcrest, Houston, Tex. 77096

[21] Appl. No.: 687,107

[22] Filed: Jul. 22, 1996

Related U.S. Application Data

[63] Continuation-in-part of Ser. No. 567,929, Dec. 6, 1995, abandoned.

[51] Int. Cl.$^6$ .............................. A61N 1/05; A61N 1/372
[52] U.S. Cl. .......................... 607/122; 607/9; 607/10; 607/27; 607/119
[58] Field of Search .................... 607/9, 10, 119, 607/122, 126, 27

[56] References Cited

U.S. PATENT DOCUMENTS

| | | | |
|---|---|---|---|
| 3,903,896 | 9/1975 | Harmjanz | 607/122 |
| 4,407,304 | 10/1983 | Lieber et al. | 607/122 |
| 5,111,830 | 5/1992 | Bemurat | 607/122 |
| 5,356,427 | 10/1994 | Miyata et al. | 607/122 |
| 5,480,419 | 1/1996 | Bemurat | 607/115 |
| 5,496,354 | 3/1996 | DeBellis | 607/37 |

*Primary Examiner*—William E. Kamm
*Assistant Examiner*—Carl H. Layno
*Attorney, Agent, or Firm*—David M. Ostfeld

[57] ABSTRACT

A pacemaker lead is disclosed of the type comprising a flexible cord formed of at least one spiralled electric conductor and surrounded by a sheath of insulating material and connected, at a proximal end of the lead, to a connection head removable from the pacemaker and, at a distal end, to a stimulation electrode device, where the lead is characterized by the addition of at least one opening in the sheath in the connection head that allows electrical conductive access to the spiralled conductor between the proximal and distal ends of the lead and where said opening has an associated removable closing means and where the opening is designed to be matable to an external distal lead end to make electrical contact with the conductor and to make the external lead maintain electrical contact during pacemaker implantation and replacement.

9 Claims, 5 Drawing Sheets

PACEMAKER CONNECTOR WITH SEALABLE ACCESS OPENINGS AND METHODS FOR ITS USE

CROSS REFERENCE TO RELATED APPLICATION

This application is a continuation-in-part of U.S. application Ser. No. 08/567,929, filed Dec. 6, 1995, now abandoned entitled "A Pacemaker with Sealable Access Openings and Methods for Its Use", which is incorporated herein by reference, including the drawings, for all purposes.

BACKGROUND OF THE INVENTION

1. Field Of The Invention

The present invention relates generally to pacemaker stimulation leads for use in humans and animals. More particularly, the present invention relates to the connector to the pacemaker having at least one capable access opening to a surface of the stimulation lead conducting element for connecting the lead to an external pacing unit for continuous heart stimulation during pacemaker installation or replacement.

2. Description Of The Art

Pacemakers have become a part of every day life for that segment of the community whose hearts are unable to maintain normal rate or rhythm. Pacemakers work by applying electrical stimulation to the heart muscle to stimulate efficient pumping action. The pacemaker applies periodic electrical stimulation to regulate and control the patient's heart rate and rhythm.

Conventional pacemaker installation and replacement requires the insertion through a femoral vein of a pacing lead attached to an external pacing power supply to maintain heart beat regularity during the installation and replacement procedure. The insertion of femoral pacing leads requires the use of X-ray fluoroscopy to monitor the progress of the lead through the femoral vein up to and into the heart so that the lead end can make electrical contact with the heart muscle sensitive to periodic electrical stimulation.

Most current pacemakers contain stimulation leads where only the head or proximal end of the lead receives electric stimulation from the pacemaker because only the connector at the head of the lead is inserted into the pacemaker and fixed by a pin and set screw. Adapters are available so that various suppliers of pacemakers can be used, but these are not always necessary. Thus, the leads used for electrical stimulation of a patient's heart through a distal end stimulation device implanted in the heart are only accessible when the leads are disconnected from the pacemaker and the heart then made accessible for connection of an external pacing unit. The pacing is ordinarily started or continued by the external pacing unit through a femoral lead.

During replacement of a pacemaker, the stimulation lead is usually not replaced. The operation consists of disconnecting the pacemaker-lead connector which generally involves loosening a screw providing pacemaker to lead contact through the connector and removing the lead from the pacemaker. The lead end is then inserted into a new pacemaker and the pacemaker and lead are reconnected. Again, reconnection of the pacemaker-lead connection generally involves tightening the screw on the connector head of the lead. Finally, the lead and pacemaker are implanted under the skin.

But as soon as pacemaker-lead connection is disrupted during the replacement process, the patient will no longer be receiving periodic electrical heart stimulation from the pacemaker. Such a disruption in pacing stimulation is not serious in patients whose heart is able to keep spontaneous cardiac rate or rhythm. However, in some patients, called "dependent" patients, their hearts are not capable of spontaneous cardiac rate or rhythm. A disruption in electrical stimulation to the heart in such patients could in some circumstances place those patients in some difficulty.

It is an object of the present invention to provide patients with pacemaker stimulation leads that would be amenable to the use of external electrical stimulation during installation and replacement of pacemaker to obviate the need for femorally inserted external pacing leads or the need to disrupt pacing stimulation during pacemaker replacement in a manner to minimize the potential for stimulation lead damage.

SUMMARY OF THE INVENTION

The present invention provides a pacemaker stimulation lead including a flexible cord. The flexible cord includes at least one spiralled electric conductor and a surrounding sheath of insulating material. The cord further includes a first connection means, located at a proximal end of the cord, for removably, electrically coupling the conductor to a pacemaker. The cord also includes a second means, located at a distal end of the cord for either integrally or removably, electrically coupling the conductor to an electrode stimulation device implanted in a patient's heart.

The lead also includes at least one sealable or capable access opening in the insulating sheath or preferably in the connector allowing access to a surface of the conductor of the lead between the proximal and distal ends of the lead and preferably associated with the proximal portion of the lead. The access opening or openings are used for connecting the lead to an external pacing unit and placing the external pacing unit in conductive contact with the conductor and through the conductor with the stimulation device so that the patient is in continuous stimulation during pacemaker installation or replacement. The access openings are closed with a closing member made of a non-conducting material where the opening and the closing member cooperatively form a hermetic seal when access is not needed and where the closing member does not come into direct mechanical contact with the conductor.

Preferably the opening has associated with it a conductive member affixed into the insulation of the conductor that is in electrical contact with the flexible lead and operates as the conductive surface for attaching an external lead upon removal of the closing member which is hermetically sealing the opening.

The present invention also provides for a specially designed external lead assembly for fast and efficient attachment of the external leads to at least one sealable access opening preferably in the body sheath of a pacemaker connector. The external lead assembly includes a flexible cord. The flexible cord includes at least one spiralled electric conductor and a surrounding sheath of insulating material, usually plastic. The cord further includes a first connection means for removably, electrically coupling the conductor, which is between the flexible cord and the pacemaker, to an external pacing unit. The cord also includes a second means for access for removably, electrically coupling the conductor to an internal lead conductor through an opening in the sheath surrounding the internal lead conductor, preferably in the connector, so that the external pacing unit can stimulate a patient's heart during pacemaker implantation and replacement.

The present invention also provides for a method for the installation of pacemaker assemblies of the present invention including the steps of making an incision in the patient's chest wall. At least one internal pacing lead, distal end first, is then inserted into the incision. An external pacing lead associated with an external pacing unit is attached to a sealable or capable access opening associated with the proximal portion of the internal pacing lead and preferably with the connector. The internal lead with attached external lead is then further inserted into the incision and directed through a vein into the heart so that the distal end becomes implanted into a stimulation region of the heart, usually, the right auricle and another into the right ventricle.

The external pacing unit then supplies periodic electrical stimulation to the heart, usually to the right ventricle, after implantation of the distal internal pacing lead end. A pacemaker electronic head is then connected to the proximal end of the internal pacing lead through the conductor. The external pacing unit is turned off and the internal pacemaker electronics and its enclosed battery are tested for proper periodic stimulation of the heart. After testing the internal pacemaker assembly and insuring proper operation, the external pacing lead(s) are removed from the capable access opening(s) preferably in the lead connector and the opening (s) are hermetically sealed using a closing member(s) where the closing member(s) does not make direct mechanical contact with the cord, but can make direct contact with an affixed conductive member. The incision is then sutured.

The present invention also provides for a method for the replacement of the pacemaker assemblies of the present invention including the steps of making an incision in the patient's chest wall adjacent to a sealable or capable access opening in the lead, preferably in the connector, associated with the proximal portion of the lead, removing the closing member of the sealed opening and attaching an external pacing lead to the opening so that the external lead makes electrical contact with the internal lead. The external pacing lead is associated with an external pacing unit designed to supply periodic electrical stimulation to the heart through an implanted distal internal pacing lead preferably through the connector.

The external pacing unit is then turned on to begin external heart pacing. A pacemaker electronic head is then disconnected from the proximal end or ends of the internal connector(s). A new pacemaker is then attached to the proximal end or ends of the internal connector(s). The new pacemaker is then tested for heart regulation and stimulation by turning off the external unit and monitoring the new pacemaker. Once the testing of the new pacemaker and its battery are complete, the external lead is disconnected from the opening and the closing member is reattached to the opening to form a hermetic seal. The incision is then sutured.

BRIEF DESCRIPTION OF THE DRAWINGS

For a further understanding of the nature and objects of the present invention reference should be made to the following Drawings, in which, like parts are given like reference numerals and wherein.

DETAILED DESCRIPTION OF THE PREFERRED AND ALTERNATE EMBODIMENT

Figure 1:
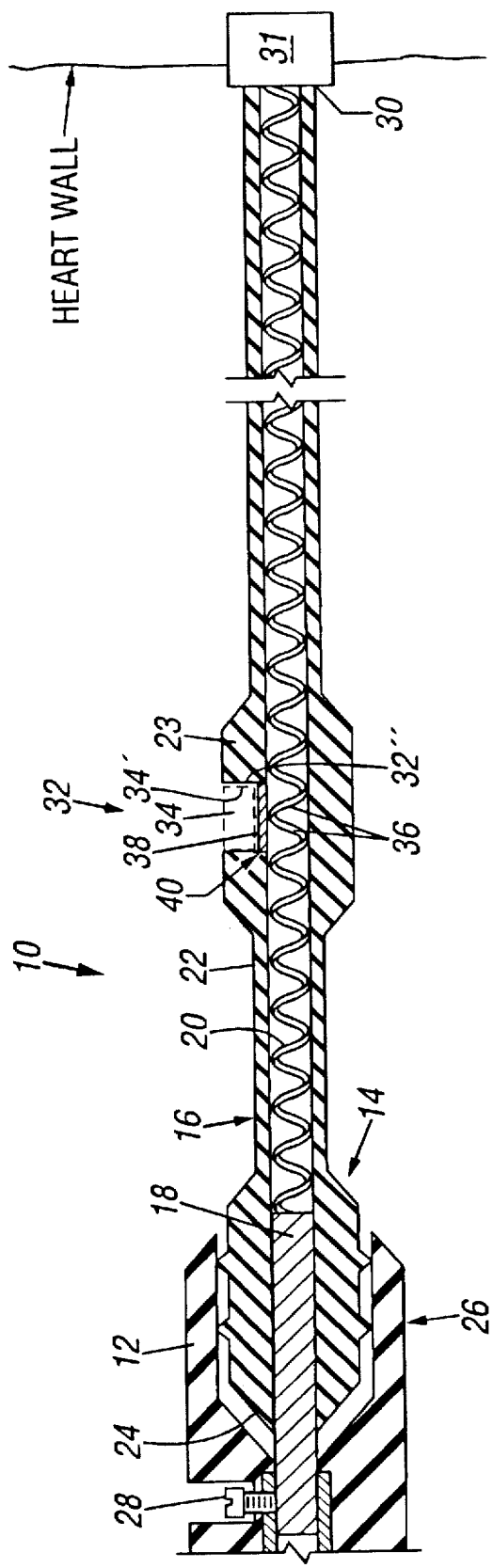
FIG. 1 is an axial sectional view of a flexible cord in accordance with the invention, in a first embodiment depicting a unipolar lead and with one capable opening.

By adding sealable or capable access openings located between the ends of a pacing lead and preferably associated with the proximal portion of an internal pacing lead, a superior pacemaker lead, especially if the openings are in the connector, can be constructed that will obviate the need for the use of femoral external pacing leads during pacemaker installation and replacement. The addition of at least one access opening in the lead will decrease the surgical time for installation and replacement of pacemakers and reduce the exposure of patients to X-rays during pacemaker installation and replacement.

Additionally, using an external lead with a specialized end for attaching the external lead to the internal lead opening also aids in implantation and replacement of pacemakers. The specialized lead end insures that the external lead is in electrical contact with a conducting cord of the lead and that the external lead is held in place during pacemaker implantation or replacement to avoid pacing stimulation disruption to a patient's heart.

The lead of the preferred embodiment of the present invention comprise a flexible cord. As used in this invention, a flexible cord is a flexible insulated, electrically conductive element connecting a stimulation electrode device to a pacemaker. The cord can be a single flexible element or a plurality of flexible elements. The cord can also be a flexible element connected to any interconnection means such as a so-called adapter connection having an appropriate head for mating with the sockets of a pacemaker or stimulation electrode.

The openings of the preferred embodiment of the present invention are situated along the length of the element and preferably on a proximal portion of the element at the connector. The closing members of the preferred embodiment of the present invention are associated with the opening to form a removable, hermetic seal over the opening. By removing the closing member from the opening, an external conductive element associated with an external flexible lead can be brought into conductive contact with the conductive element of the internal cord. The electric contact provides a pathway for external stimulation of the heart during pacemaker implantation and replacement without the need for femoral vein pacing leads.

With such pacemaker lead having access opening along the length of the conductive element, at the time of implanting or changing the pacemaker, the closing member can simply be removed, by either unscrewing, unsnapping, retracting, or other means for removing, from the opening giving access to the internal conductor of the lead. An external lead end can then be inserted into the opening to make the necessary electrical contact with the conductive element in the internal lead. After connecting the external lead to an auxiliary (external) stimulation unit, the internal lead may be disconnected from the pacemaker without risk to the patient.

Once the pacemaker or new pacemaker is positioned and tested, the auxiliary lead end is disengaged from the opening of the internal lead and the closing member is re-inserted into the opening to hermetically seal the opening from the body. Thus, the cardiac stimulation of the patient is substantially continuous during the whole operation and pacemaker testing. In addition, the opening may be associated with a thickened portion of the surrounding insulator or sheath to facilitate efficient removal and reattachment of the closing member.

In FIG. 1, a pacemaker and lead assembly, generally 10, of one, non-preferred embodiment of the present invention has been shown schematically, partially, and in cross-section. A pacemaker 12 (partially shown) has inserted therein a proximal end 14 of a unipolar lead, generally 16, having a head element 18 associated with the proximal end 14.

The unipolar lead 16 is composed of an electric conductor 20 preferably wound in a spiral and more particularly where the windings have substantially jointing turns. The conductor 20 is in turn surrounded by an insulating sheath 22 made from a flexible electrically insulating and bio-compatible material such as polyurethane, polyethylene, polybutylene, polyhexene, and other similar bio-compatible polymers. The combination of the spiral wound conductor 20 and the flexible insulating material 22 insures that the entire lead 16 is flexible for easy insertion and positioning within a patient's heart.

Generally, the conductor 20 terminates at the head element 18 partially enclosed in a male tubular fitting 24 intended to be inserted into a mated female tubular socket 26 associated with the pacemaker 12 so that the conductor 20 is brought into electric contact with the internal circuitry of the pacemaker 12 through the head element 18. The head element 18 and socket 24 are generally held secure in the pacemaker socket 26 via a screw 28 or by any other similar securing device or means that frictionally engages the head element 18.

The distal end 30 of lead 16 having conductor 20 is in turn connected to a unipolar or bipolar electrode stimulation device 31 which is implanted into the patient's heart to supply pacing stimulation signals generated by the pacemaker 12 to the heart.

According to the present invention, at a given position along the lead 16, at least one opening 32 is provided in the sheath 22, preferably in the less flexible sheath 220 of connector 230 (FIG. 8), making the internal conductor 20 accessible for external connection. Preferably, the opening 32 is located in a proximal portion of the lead 16 where "proximal portion" means that the opening is located between the proximal end 14 and a mid point of the length of the lead 16. The opening 32 has associated with it a closing member 34 (shown in phantom in FIG. 1) which inserts into the opening 32 to form a hermetic seal to fully isolate an accessible portion 36 of the conductor 20, made accessible by the opening 32 in the sheath 22, 220, surrounding the conductor 20 from body fluids which could possibly cause a short circuit. Preferably, the opening 32 is associated with a thickened region 23 of the sheath 22, 220 to facilitate removal and reattachment of the closing member 34 to the opening 32.

In the embodiment illustrated in FIG. 1, the opening 32 in the sheath 22, 220 comprises an essentially circular opening. However, the opening can be of any other convenient shape such as oval, square, rectangular, and the like. Additionally, the opening can be tapered, e.g., the opening in the surface of the sheath 22, 220 can be larger or smaller than the opening that provides electrically conductive access to the internal lead conductor 20.

Figure 7:
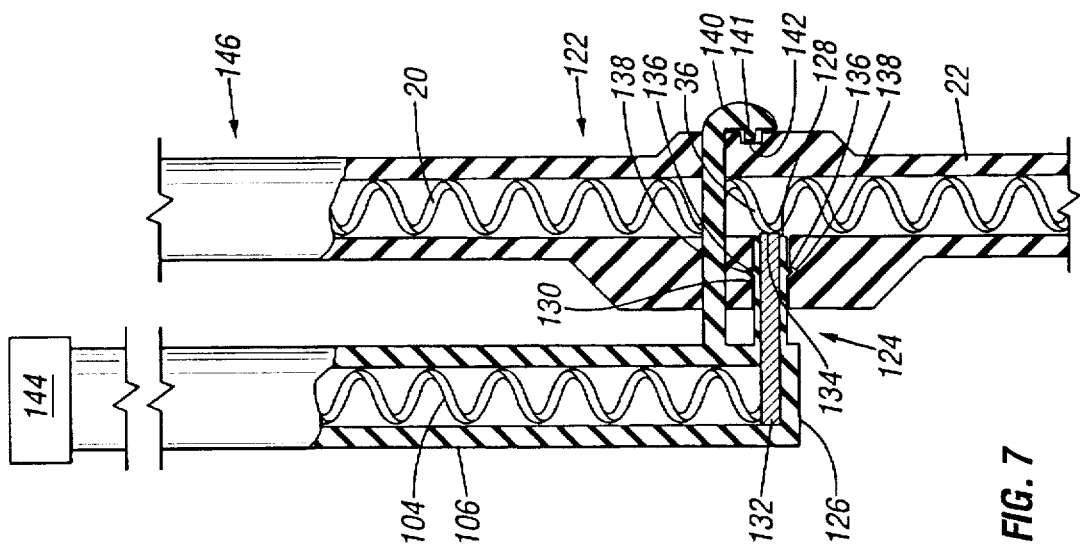
FIG. 7 depicts a sectional view of another embodiment of an external lead end adapted to attach to the opening in the internal leads of the invention and anchor the external lead to the internal lead.
Figure 6:
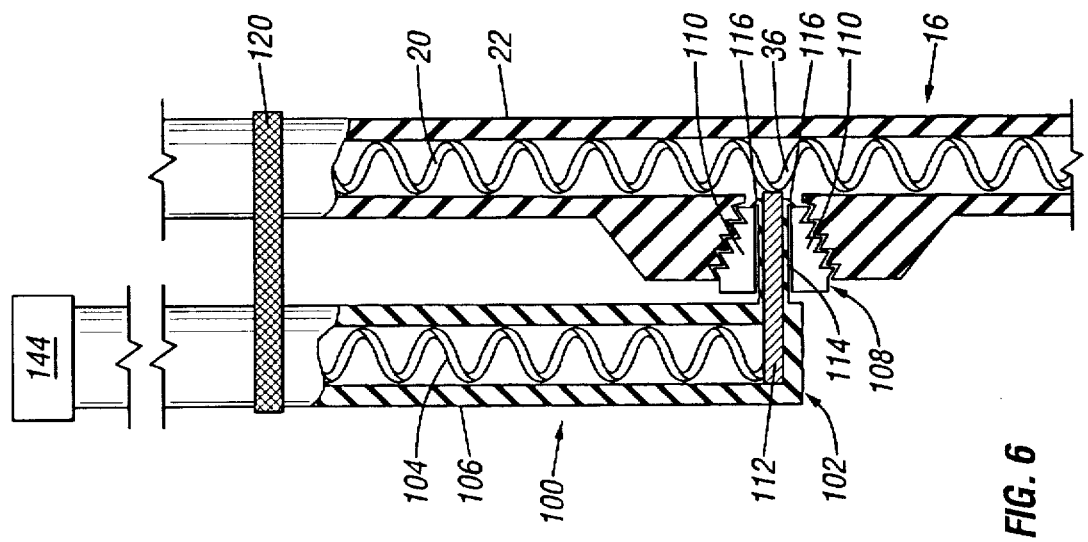
FIG. 6 depicts a sectional view of one embodiment of an external lead end adapted to attach to an opening in the internal leads of the invention.

The opening 32 is generally of a size sufficient to permit an external lead end 102 associated with an external lead 100, non-limiting examples of which are shown in FIGS. 6 and 7 and described subsequently, to be inserted therein and make electrical contact with the accessible portion 36 of the conductor 20. The size of the opening will generally be several millimeters (between about 2 to about 10 mm) in diameter or in its widest dimension if the opening is non-circular. The opening can be smaller or larger and is limited only by ease of manufacturing and use in practice.

Figure 2:
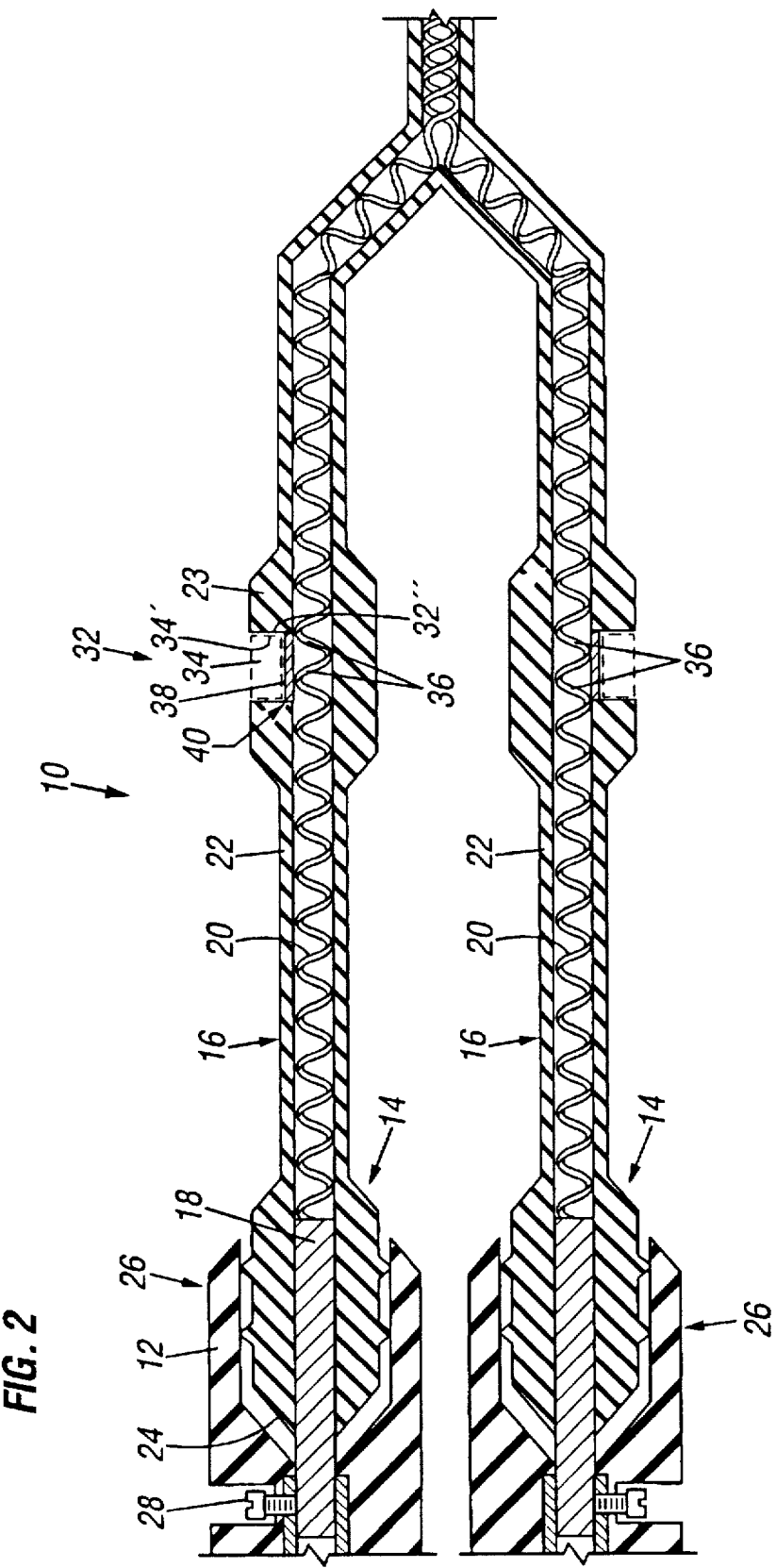
FIG. 2 illustrates an axial sectional view of bi-polar leads of the invention having one capable opening in each lead.
Figure 8:
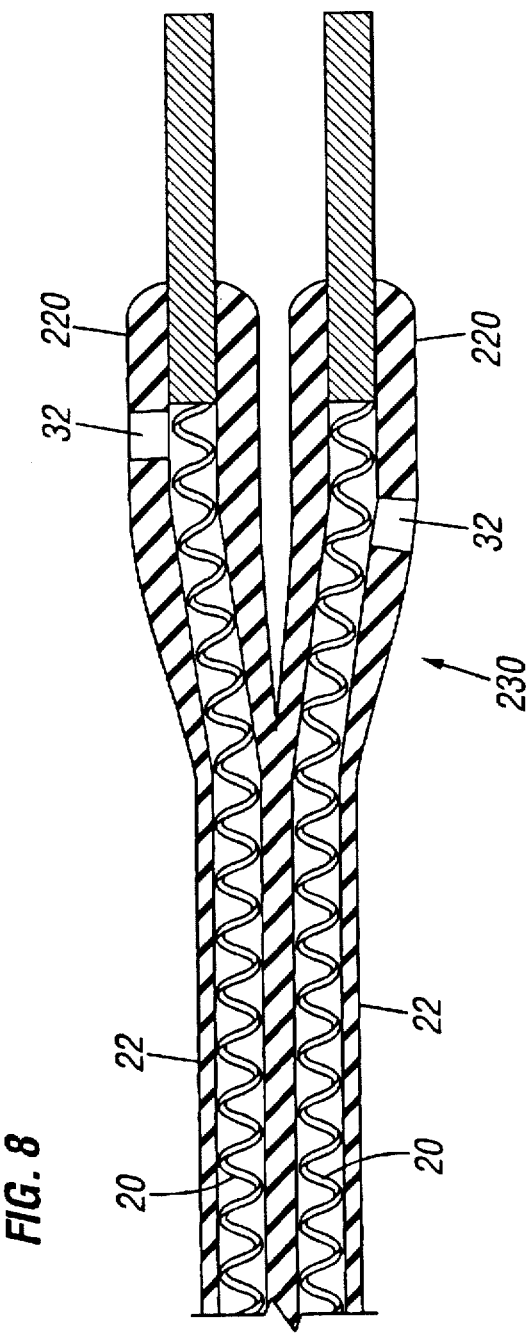
FIG. 8 depicts a sectional view of the preferred embodiment of bi-polar leads of the invention having one capable opening in the connector of each lead.

In the case of a bi-polar lead construction, at least one opening would be associated with each conductive element in the bi-polar lead as shown in FIG. 2 or FIG. 8 where the numbering is consistent with the number in FIG. 1, as applicable, except that there are two leads, two conductive elements, two openings, and two closing members.

Optionally, the leads of the present invention can also include a conductive plate or electrode 38 at a bottom 40 of the opening 32. The electrode 38 can be either secured in the opening 32 by conventional means such as pressing or the like provided it is in electrical contact with the accessible portion 36 of the conductor 20 or can be affixed to the accessible portion 36 of the conductor 20 by conventional means such as welding, soldering, or the like, prior to sheath construction. The electrode or plate 38 serves to protect the accessible portion 36 of the conductor 20 from possible damage during the external lead connection process and to provide a larger, and more well defined, surface for achieving electrical contact between an external lead end 102 and the conductor 20. Of course, the plate or electrode 38 should be constructed in such as way as not to adversely affect the overall flexibility of the lead 16 needed for the internal passage of the lead 16 into the heart or repositioning the lead 16.

When the opening 32 does not have an associated conductive plate or electrode 38, it is preferred that the closing member 34 be sized so that when it is secured in the opening 32 there is a gap between the bottom of the closing member 34 and the accessible portion 36 of the conductive element 20. That is, in the absence of a conductive electrode 38, the closing member 34 should be constructed so as not to make direct mechanical contact with the accessible portion 36 of the conductive element 20 of the internal lead 16. Such a gap is represented by the area designated by numeral 39 where the plate 38 would otherwise be, as is shown in FIGS. 1 and 2.

In the leads of the present invention, it is preferably, that the external lead 100 have associated with it a specialized distal end 102, as illustrated in FIGS. 6 and 7 and described below, that is matable with the opening 32 and affixes the external lead 100 to the internal lead 16 so that external stimulation can be supplied to the patient's heart even after disconnection of the internal lead 16 from the pacemaker 12.

In the normal state of assembly 10, the internal lead 16 is connected to the pacemaker 12 and the opening 32 is sealed with the closing member 34 as shown in FIGS. 1 and 2 where the "normal" position of the closing member 34 inserted into opening 32 has been shown in phantom with broken lines at 34'.

The role of closing member 34, which can be made, for example, from the same material as sheath 22, 220 or any other bio-compatible material, is to electrically insulate and isolate the accessible portion 36 of the conductor 20 from the medium surrounding the lead 16. The closing member 34 must sealingly engage the opening 32 because the pacemaker and the proximal portion of the flexible cord are disposed under the skin of the patient and are likely to be in contact with a conducting medium. This contact could cause short circuit between the spiralled conductor 20 and the pacemaker 12, which should be avoided, except through screw 28.

The closing member 34 should be relatively easy to insert in and affix to the opening 32; therefore, in order to have sealing as perfect as possible, the opening 32 will have associated with it a means for affixing or anchoring the closing member 34 in the opening 32 to make the sheath 22, 220 a contiguous and continuous insulator for the conductor 20. Those same means for affixing or anchoring the closing member 34 inside the opening 32 apply equally well for anchoring the external lead 100 in the opening 32 so that the external lead conductor 104 makes electrical contact with the accessible portion 36 of the conductor 20 when the external lead end 102 is inserted into the opened opening 32 as shown in FIGS. 6 and 7.

Figure 3:
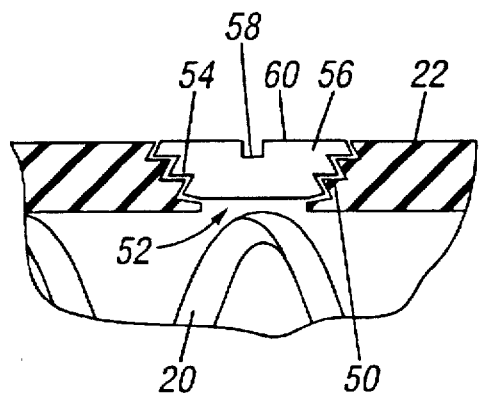
FIG. 3 depicts an enlarged sectional view of one embodiment of an opening and closing member of a capable opening of the invention.
Figure 4:
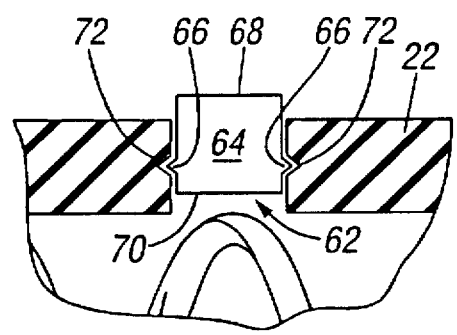
FIG. 4 depicts an enlarged sectional view of a second embodiment of an opening and closing member of a capable opening of the invention.
Figure 5:
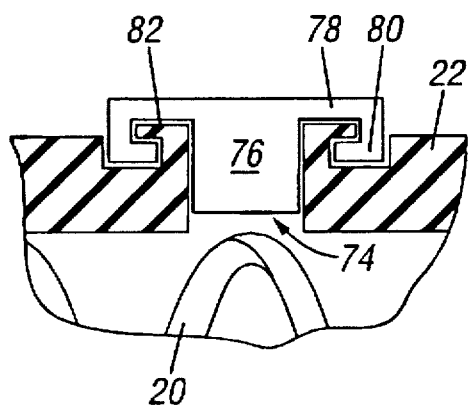
FIG. 5 depicts an enlarged sectional view of a third embodiment of an opening and closing member of a capable opening of the invention.

The means for anchoring, which while indicated for sheath 22 in the drawings is equally applicable to conductor sheath 220, can be any means for anchoring a conductor in an opening that are known in the art. Several illustrative embodiments of the anchoring means are shown in FIGS. 3-5. Referring to FIG. 3, the anchoring means comprises threads 50 (shown generally as "32'" in FIGS. 1 and 2) in the portion of the sheath associated with the opening 52 (shown generally as "32" in FIGS. 1 and 2) and mating threads 54 (shown generally as "34'" in FIGS. 1 and 2) associated with the closing member 56 (shown generally as "34" in FIGS. 1 and 2) to allow the closing member 56 to be threaded into the opening 52.

Additionally and preferably, the closing member 56 of FIG. 3 has a removal slot or indentation 58 in a top 60 of the closing member 56. The removal slot or indentation 58 can be a standard type screw driver slot as shown in the figure, a Phillips type screwdriver indentation, a polygonal indentation or any other similar slot or indentation that will allow the closing member 56 to be quickly and easily unscrewed from the opening 52.

Referring to FIG. 4, another opening 62 (shown generally as "32" in FIGS. 1 and 2) and closing member 64 (shown generally as "34" in FIGS. 1 and 2) configuration is shown which comprises a raised flange 66 (shown generally as "34'" in FIGS. 1 and 2) associated with the closing member 64 where the flange 66 is located sufficiently removed from a top 68 and a bottom 70 of the closing member 64 so that the flange 66 will secure the closing member 64 in the opening 62 by securably engaging a receiving annular indentation 72 (shown generally as "32'" in FIGS. 1 and 2) in sheath 22, 220 defining the opening 62. The reverse configuration is also equally acceptable, i.e., where the flange 66 is associated with the sheath 22, 220 and the annular indentation 72 is associated with the closing member 64.

Referring now to FIG. 5, yet another opening 74 (shown generally as "32" in FIGS. 1 and 2) and closing member 76 (shown generally as "34" in FIGS. 1 and 2) configuration is shown where the closing member 76 includes a top portion 78 having associated therewith a lip 80 (shown generally as "34'" in FIGS. 1 and 2) for securing the closing member 76 to the sheath opening 74 through the presence of a annular locking indentation 82 (shown generally as "32'" in FIGS. 1 and 2) encircling the opening 74. The lip 80 of the closing member 76 is designed to be snapped into indentation 82 formed in the sheath 22, 220 to hold the closing member 76 and form a hermetic seal with the sheath 22, 220.

For ease of use and expediency in external lead attachment, the present invention also contemplates external leads with specially designed ends to facilitate external lead attachment and anchoring to the openings in the internal lead of the invention. Referring to FIG. 6, a external lead, generally 100, with one such specialized distal end 102, is shown. The external lead 100 includes a conductor 104, preferably spiralled, surrounded by a flexible sheath 106 where the conductor and sheath are similar or identical to the conductor and sheath described for the internal leads 16 above. The specialized distal end 102 of the external lead 100 comprises a perpendicularly disposed head member 108 which is designed to engage the opening 32 in the internal lead 16 in accordance with the type of opening 32 utilized in the lead 16.

Three possible opening designs were described in association with FIGS. 3-5. For the purpose of FIG. 6, the head member 108 includes a threaded rotatable sleeve 110 for securingly engaging the threaded opening 52 of FIG. 3. The head member 108 further includes a conductive head element 112 surrounded by a sheath 114 (which can be integral with the sheath 22, 220 or hermetically attached to the sheath 22, 220) having a sleeve retaining flange 116 associated therewith where the sheath 114 is interposed between the sleeve 110 and the head element 112 and where the head element 112 is designed to either conductively engage the accessible portion 36 of the conductor 20 of the lead 16 or the plate 38 which can be optionally associated with opening 32 and the accessible portion 36 of the conductor 20. Of course, the head member 108 will vary in construction depending on the type of closing member 34 used in the construction of the leads 16 of the present invention. However, the end 102 will include a means for attaching the external lead 100 to the opening 32 of the internal lead 16 and a conductive head element inserted through the attaching means designed to make electrical contact with the conductive element 20 in the internal leads 16 of the invention.

Moreover, the external leads of the present invention can also include one or more securing elements 120 for securing the external lead 100 to the internal lead 16 after the external lead end 102 has been mated with the opening 32 in the internal lead 16. Such securing elements 120 can be plastic clips that are designed to hold the leads 16, 100 in close parallel proximity as shown in FIG. 6 or the end 102 of the external lead 100 can be of a clippable design, generally 122, as shown in FIG. 7.

The clippable end 122 of FIG. 7 includes an opening engagement assembly 124 mounted on a distal end 128 of a first arm 126 of the end 122. The assembly 124 includes an attaching member 130 and a conductive head element 132 passing therethrough and where a distal end 134 of the head element 132 is designed to electrically engage the accessible portion 36 of the conductive element 20. The attachment member 130 of FIG. 7 is equivalent in structure to the closing member 64 of FIG. 4 and where the member 130 has a flange 136 designed to engage an indentation 138 in the sheath 22, 220. The clippable end 122 further includes a second arm 140 which engages the opposite side of the sheath 22, 220 from the opening 32. The second arm 140 can include a knob or raised portion 141 designed to fit into a indentation 142 in the sheath 22, 220 opposite the opening 32. This embodiment of the external lead end 102 can also include securing clips 120 as described above. Additionally, the external leads 100 of the present invention are designed to electrically engage an external pacing unit 144 at a proximal end 146 of the external leads 100 in any manner well known to in the art.

For the preferred embodiment as shown in FIG. 8, by avoiding the flexible sheath 22 and using the sheath 220 of the less flexible connector 230 for access to conductive element 20, one minimizes the probability of damage to the conductive element 20 during flexing of conductive element 20 for insertion into opening 32. Second, by using connector 230, there is immediate access, without needing to locate the opening 32 which may otherwise be concealed by an overgrowth of body tissue which might require dissection. Also, locating opening 32 in connector 230 lowers the likelihood of the cover 34 sliding during the normal movements of the patient while he or she is using the pacemaker. Also, there is less potential of the cover 34 to be stuck in place for free access. In addition, there is a lesser likelihood that the conductive element 20 would be fractured while working with a connection to an external generator 144 or preparing to attach an external generator 144. In addition, by placing access openings 32 in connectors 230, the position of the openings 32 could identify the positive and negative conductive elements 20 through their positioning, such as opening 34 to the positive could be placed proximally, and opening 34 to the negative could be placed posteriorly (see FIG. 8). Finally, where two conductive elements 20 are used, the two conductors are ultimately separated by insulation, but are wound in spiral fashion around each other, as shown in FIG. 2. By using the connector 230 of the preferred embodiment, the conductive elements 20 are already separated making access easier and thus further avoiding damage to the flexible part of the conductive element 20.

The present invention also discloses a method for the installation or implantation of pacemakers in a patient taking advantage of the use of an external pacing unit to supply pacing stimulation directly through the lead being implanted. The method generally includes the steps of making an incision in the patient's chest wall. A sealing member 34 is removed from a sheath 22, 220 surrounding a conductive element 20 of an internal pacing lead 16 to reveal an opening 32 to a portion 36 of a conductive element 20 in the internal lead 16. The conductive element 20 of the lead 16 is insulated from body fluids by a surrounding biocompatible sheath 22. The opening 32 is defined in the sheath 22, 220 and provides access to the internal lead conductor 20 at the portion 36 so that an external pacing lead 100 can be attached to the internal lead 16 making electrical contact with the internal conductor 20 at the portion 36. Optionally, the external lead 100 can be clipped to the internal lead 16 with an appropriate clipping devices 120 to ensure that the external lead 100 remains attached to the internal lead 16 during insertion. With the external lead 100 attached, an external pacing unit 144 can supply pacing stimulation to the internal lead 16 so that heart stimulation can be immediately supplied to the patient's heart during implantation.

Once the external lead 100 is attached to the internal lead 16 and placed in electrical contact with its internal lead conductor 20 at the portion 36, a distal end 30 of at least one internal pacing lead 16 of the present invention having a heart stimulation electrode device 31 attached thereto is then inserted into the incision. The internal lead 16 with attached external lead 100 is then further inserted into the incision and the distal end 30 of the internal lead 16 directed into the heart through a vein so that the heart stimulation electrode device 31 becomes implanted into a region of the heart amenable to external stimulation.

The external pacing unit 144 supplies periodic electrical stimulation to the heart after implantation of the distal internal pacing lead end 30 and associated stimulation device 31. The pacemaker electronic head 12 with its enclosed battery is then connected to a proximal end 14 of the internal pacing lead 16. The external pacing unit 144 is turned off and the internal pacemaker electronics and battery are tested for proper periodic stimulation of the heart. After testing the internal pacemaker 12 and insuring proper operation, the external pacing lead or leads 100 (one lead in the case of a unipolar pacemaker or two leads in the case of a bi-polar pacemaker) are removed from the capable access opening(s) 32 in the lead insulation 22, 220 of the internal lead 16, and the opening(s) 32 are hermetically sealed using one closing member 34 for each opening 32. The incision is then sutured.

The present invention also provides for a method for the replacement of pacemakers. An incision is made in a patient's chest wall adjacent to a sealable or capable access opening 32 in a lead sheath 22, 220 of an internal pacing lead 16 where the opening 32 is preferably associated with a proximal portion of the lead 16 and where the sheath 22 surrounds a conductive element 20 of the internal lead 16.

Once the incision is made, a closing member 34 associated with the sealed opening 32 is removed. With the closing member 34 removed, an end 102 of an external pacing lead or leads 100 are inserted into the opening 32 so that the external pacing lead or leads 100 make electrical contact with an accessible portion 36 of the conductor 20 of the internal lead 16. The external pacing lead 100 is electrically associated with an external pacing unit 144 designed to supply periodic electrical stimulation to the heart through internal lead 16 to the implanted distal internal pacing lead end 30 with its associated stimulation device 31.

The external pacing unit 144 is then turned on to begin external heart pacing. A pacemaker 12 with its enclosed battery is then disconnected from the proximal end 14 of the internal lead 16. (In the case of a bi-polar pacemakers, two external leads are disconnected.) A new pacemaker 12 is then attached to the proximal end or ends 14 of the internal lead(s) 16. The new pacemaker 12 is then tested for heart regulation and stimulation by turning off the external unit 144 and monitoring the new pacemaker's operation.

Once the testing of the new pacemaker 12 is complete, the external lead 100 is disconnected from the opening 32 and the closing member 34 is reattached to the opening 32 to form a hermetic seal. The incision is then sutured.

Finally, the invention is obviously not limited to the embodiments shown and described above but covers on the contrary all variants thereof, particularly in so far as the means are concerned giving access to the spiralled conductor and the mobile means combined with said access means for providing access at will to said conductor or on the contrary total electric and sealed insulation thereof with respect to the environment in which the lead is plunged.

All of the features of a particular preferred embodiment of the pacemaker lead are not shown in the above disclosure in order to emphasize the generality of the disclosure.

Because many varying and different embodiments may be made within the scope of the invention concept taught herein which may involve many modifications in the embodiments herein detailed in accordance with the descriptive requirements of the law, it is to be understood that the details herein are to be interpreted as illustrative and not in a limiting sense.

I claim:

1. A pacemaker coupling for use with an internal pacing unit and an electrode stimulation device comprising:
   a flexible cord which includes:
   a) at least one spiraled electric internal conductor;
   b) a sheath of insulating material surrounding said conductor;
   c) a connector at a proximal end of said cord;
   d) a first connection means located at said proximal end of said connector for removably, electrically coupling said conductor to the internal pacing unit;
   e) a second means located at a distal end of said connector for electrically coupling the conductor to the electrode stimulation device;
   f) at least one sealable access orifice in said distal portion of said connector, said orifice extending to a portion of said conductor;
   g) a closing member having means for cooperatively engaging said orifice to form an hermetic seal;
   wherein there is a second conductor and a second orifice extending to a portion of said second conductor, said second orifice comprises an opening located on a distal portion of said connector.

2. A pacemaker coupling for use with an internal pacing unit and an electrode stimulation device for use with an external pacing unit having at least one external lead comprising:
   a flexible cord which includes:
   a) at least one spiraled electric internal conductor;
   b) a sheath of insulating material surrounding said conductor;
   c) a connector at a proximal end of said cord;
   d) a first connection means located at said proximal end of said connector for removably, electrically coupling said conductor to the internal pacing unit;
   e) a second means located at a distal end of said connector for electrically coupling the conductor to the electrode stimulation device;
   f) at least one sealable access orifice in said distal portion of said connector, said orifice extending to a portion of said conductor;
   g) a closing member having means for cooperatively engaging said orifice to form an hermetic seal;
   a third means for fast and efficient attachment of the external lead to said orifice, said third means having a second flexible cord which includes:
   h) at least one spiralled electric external conductor;
   i) a second sheath of insulating material surrounding said external conductor;
   j) a first external lead connection means located at a proximal end of said external cord for removably, electrically coupling said external conductor to the external pacing unit, and
   k) second means located at a distal end of said external cord for removably, electrically coupling said external conductor to said internal conductor through said orifice, whereby the external pacing unit can stimulate a patient's heart during pacemaker implantation and replacement.

3. An external coupling for use with an external pacing unit, comprising:
   a flexible cord which includes
   a) at least one spiralled electric first conductor;
   b) a sheath of insulating material surrounding said first conductor;
   c) first connection means located at a proximal end of said cord for removably, electrically coupling said first conductor to the external pacing unit;
   an internal pacing lead which includes
   d) second conductor, a second sheath of insulating material surrounding said second conductor, a connector located at the proximal end of said second conductor, said connector including a portion of said second sheath, and an sheath portion of said connector, said orifice extending to a portion of said second conductor; and
   e) second connection means, located at a distal end of said cord, for removably, electrically coupling said first conductor to said second conductor through said orifice.

4. The external coupling of claim 3, wherein said second connection means includes an attachment fitting for securing said first conductor in said orifice of said connector and an electrode connected to said first conductor and passing through said attachment fitting for establishing electrical contact between said first conductor and said second conductor through said portion of said second conductor accessible through said orifice.

5. A method for the installation of the pacemaker assembly using an external pacing unit, comprising the steps of:
   a) inserting at least one internal pacing lead distal end with a heart stimulation electrode attached thereto into an incision in a patient's chest;
   b) attaching one external pacing lead to the internal lead through an access opening in the distal end of the connector of the internal lead so that the external lead makes electrical contact with an internal lead conductor of the internal lead allowing the external pacing unit to stimulate the patient's heart during pacemaker implantation upon activation of the external pacing unit;
   c) inserting the internal lead with the associated external lead further into the incision and directing the distal end of said internal lead into the heart so that the heart stimulation electrode associated with the distal end becomes implanted into a patient's heart through which pacing stimulation to said heart can be achieved;
   d) supplying periodic electrical stimulation through the external pacing unit to the heart after implantation of the distal internal pacing lead end electrode;
   e) connecting a pacemaker electronic head and associated battery to a proximal end of the connector of the internal pacing lead;
   f) interrupting the externally supplied electrical stimulation to test said internal pacemaker and battery for proper periodic stimulation of said heart;
   g) testing the internal pacemaker and battery;
   h) after successful testing, removing the external pacing lead from the access opening in the connector;
   i) capping the opening with a closing member to form an hermetic seal so that the internal lead conductor is electrically insulated from the patient's bodily fluids;
   wherein the attaching of the external lead to the internal lead of step (b) is through an opening located on a proximal portion of the connector; and
   wherein there is a second external lead attached to a second internal lead for step (b), such attaching being through a second opening located on a distal portion of the connector.

6. A method for replacing a pacemaker assembly using an external pacing unit, comprising the steps of:
   a) accessing one or more closing members of sealed access openings in one or more proximal end connectors for one or more internal leads having internal lead conductors through an incision in a patient's chest, where one or more distal ends with associated heart stimulation electrodes are implanted in a patient's heart so that the heart can be periodically stimulated by the pacemaker assembly;
   b) removing the closing members from the openings in the internal leads;
   c) inserting a distal end of an external pacing lead into the opening in each internal lead so that the external lead is in electrical contact with the internal lead conductor;
   d) connecting a proximal end of the external pacing leads into the external pacing unit so that periodic electrical stimulation can be supplied through the external and internal leads to the patient's heart;
   e) turning on the external pacing unit to begin external heart pacing;
   f) disconnecting the proximal ends of the internal leads from a pacemaker electronic head;
   g) removing the old pacemaker through the incision;
   h) inserting a new pacemaker into the patient through the incision;
   i) interrupting the externally supplied electrical stimulation to test the new internal pacemaker for proper periodic stimulation of the heart;
   j) testing the new internal pacemaker;
   k) after successful testing, removing the external pacing leads from the access openings in the connectors; and
   l) capping the openings with the closing members to form an hermetic seal so that the internal lead conductors are electrically insulated from the patient's bodily fluids.

7. The method of claim 6, wherein the accessing of step (a) is to one opening located on a proximal portion of the connector.

8. The method of claim 7, wherein the accessing of step (a) is to a second opening located on a distal portion of the connector.

9. The method of claim 6, wherein the capping of step (l) is such that the closing members do not come into direct mechanical contact with the conductors.

* * * * *